(12) United States Patent
Chinnaiyan et al.

(10) Patent No.: US 7,968,294 B2
(45) Date of Patent: Jun. 28, 2011

(54) SLIT2 UNDEREXPRESSION IN METASTATIC PROSTATE CANCER

(75) Inventors: Arul M. Chinnaiyan, Plymouth, MI (US); Jindan Yu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/388,058

(22) Filed: Feb. 18, 2009

(65) Prior Publication Data

US 2010/0055688 A1 Mar. 4, 2010

Related U.S. Application Data

(60) Provisional application No. 61/029,636, filed on Feb. 19, 2008.

(51) Int. Cl.
*C12Q 1/68* (2006.01)
*G01N 33/53* (2006.01)
*G01N 33/574* (2006.01)

(52) U.S. Cl. .............................. 435/6; 435/7.1; 435/7.23

(58) Field of Classification Search ........................ None
See application file for complete search history.

(56) References Cited

U.S. PATENT DOCUMENTS

2006/0024692 A1 2/2006 Nakamura et al.

OTHER PUBLICATIONS

Hui et al (Annual Report Prepared for the US Army Medical Research and Material Command, Grant No. W81XWH-04-1-0185, (Feb. 1, 2005), Fort Detrick, MD, p. 4-9 (IDS)).*
Dallol et al (Cancer Research, 2002, 62:5874-5880, IDS).*
Hui, Xu, et al.; "Enhancement of Tumor Immunotherapy by Blockade of a Prostate Tumor Derived Immunosuppressive Factor;" Grant No. W81XWH-04-1-0185; Annual Report Prepared for the U.S. Army Medical Research and Material Command, (Feb. 1, 2005), Fort Detrick, Maryland; pp. 4-9.
Dallol, Ashraf, et al.; "SLIT2, a Human Homologue of the *Drosophila* Slit2 Gene, Has Tumor Suppressor Activity and is Frequently Inactivated in Lung and Breast Cancers"; Cancer Research, (Oct. 15, 2002); vol. 62; (pp. 5874-5880).

* cited by examiner

*Primary Examiner* — Laura B Goddard
(74) *Attorney, Agent, or Firm* — Casimir Jones, S.C.

(57) ABSTRACT

This invention relates to compositions and methods for cancer diagnosis, research and therapy, including but not limited to, cancer markers. In particular, this invention relates to SLIT2 cancer markers that are useful as diagnostic markers and clinical targets for prostate cancer.

7 Claims, 10 Drawing Sheets

Figure 6

SEQ ID NO:1

```
   1 cagagcaggg tggagagggc ggtgggaggc gtgtgcctga gtgggctcta ctgccttgtt
  61 ccatattatt ttgtgcacat tttccctggc actctgggtt gctagccccg ccgggcactg
 121 ggcctcagac actgcgcggt tccctcggag cagcaagcta agaaagccc ccagtgccgg
 181 cgaggaagga ggcggcgggg aaagatgcgc ggcgttggct ggcagatgct gtccctgtcg
 241 ctggggttag tgctggcgat cctgaacaag gtggcaccgc aggcgtgccc ggcgcagtgc
 301 tcttgctcgg gcagcacagt ggactgtcac gggctggcgc tgcgcagcgt gcccaggaat
 361 atcccccgca acaccgagag actggattta aatggaaata acatcacaag aattacgaag
 421 acagattttg ctggtcttag acatctaaga gttcttcagc ttatggagaa taagattagc
 481 accattgaaa gaggagcatt ccaggatctt aaagaactag agagactgcg tttaaacaga
 541 aatcaccttc agctgtttcc tgagttgctg tttcttggga ctgcgaagct atacaggctt
 601 gatctcagtg aaaaccaaat tcaggcaatc ccaaggaaag ctttccgtgg ggcagttgac
 661 ataaaaaatt tgcaactgga ttacaaccag atcagctgta ttgaagatgg ggcattcagg
 721 gctctccggg acctggaagt gctcactctc aacaataaca acattactag actttctgtg
 781 gcaagtttca accatatgcc taaacttagg acttttcgac tgcattcaaa caacctgtat
 841 tgtgactgcc acctggcctg gctctccgac tggcttcgcc aaaggcctcg ggttggtctg
 901 tacactcagt gtatgggccc ctcccacctg agaggccata atgtagccga ggttcaaaaa
 961 cgagaatttg tctgcagtgg tcaccagtca tttatggctc cttcttgtag tgttttgcac
1021 tgccctgccg cctgtacctg tagcaacaat atcgtagact gtcgtgggaa aggtctcact
1081 gagatcccca caaatcttcc agagaccatc acagaaatac gtttggaaca gaacacaatc
1141 aaagtcatcc ctcctggagc tttctcacca tataaaaagc ttagacgaat tgacctgagc
1201 aataatcaga tctctgaact tgcaccagat gctttccaag gactacgctc tctgaattca
1261 cttgtcctct atggaaataa aatcacagaa ctccccaaaa gtttatttga aggactgttt
1321 tccttacagc tcctattatt gaatgccaac aagataaact gccttcgggt agatgctttt
1381 caggatctcc acaacttgaa ccttctctcc ctatatgaca acaagcttca gaccatcgcc
1441 aaggggacct tttcacctct tcgggccatt caaactatgc atttggccca gaaccccttt
1501 atttgtgact gccatctcaa gtggctagcg gattatctcc ataccaaccc gattgagacc
1561 agtggtgccc gttgcaccag cccccgccgc ctggcaaaca aagaattgg acagatcaaa
1621 agcaagaaat tccgttgttc agctaaagaa cagtatttca ttccaggtac agaagattat
1681 cgatcaaaat taagtggaga ctgctttgcg gatctggctt gccctgaaaa gtgtcgctgt
1741 gaaggaacca cagtagattg ctctaatcaa agctcaaca aatcccgga gcacattccc
1801 cagtacactg cagagttgcg tctcaataat aatgaattta ccgtgttgga agccacagga
1861 atctttaaga aacttcctca attacgtaaa ataaacttta gcaacaataa gatcacagat
1921 attgaggagg gagcatttga aggagcatct ggtgtaaatg aaatacttct tacgagtaat
1981 cgtttggaaa atgtgcagca taagatgttc aagggattgg aaagcctcaa aactttgatg
2041 ttgagaagca atcgaataac ctgtgtgggg aatgacagtt tcataggact cagttctgtg
2101 cgtttgcttt ctttgtatga taatcaaatt actacagttg caccaggggc atttgatact
```

Figure 6 (CONT)

```
2161 ctccattctt tatctactct aaacctcttg gccaatcctt ttaactgtaa ctgctacctg
2221 gcttggttgg gagagtggct gagaagaag agaattgtca cgggaaatcc tagatgtcaa
2281 aaaccatact tcctgaaaga ataccccatc caggatgtgg ccattcagga cttcacttgt
2341 gatgacggaa atgatgacaa tagttgctcc ccactttctc gctgtcctac tgaatgtact
2401 tgcttggata cagtcgtccg atgtagcaac aagggtttga aggtcttgcc gaaaggtatt
2461 ccaagagatg tcacagagtt gtatctggat ggaaccaat ttacactggt tcccaaggaa
2521 ctctccaact acaaacattt aacacttata gacttaagta acaacagaat aagcacgctt
2581 tctaatcaga gcttcagcaa catgacccag ctcctcacct taattcttag ttacaaccgt
2641 ctgagatgta ttcctcctcg cacctttgat ggattaaagt ctcttcgatt actttctcta
2701 catggaaatg acatttctgt tgtgcctgaa ggtgctttca atgatctttc tgcattatca
2761 catctagcaa ttggagccaa ccctctttac tgtgattgta acatgcagtg gttatccgac
2821 tgggtgaagt cggaatataa ggagcctgga attgctcgtt gtgctggtcc tggagaaatg
2881 gcagataaac ttttactcac aactccctcc aaaaaattta cctgtcaagg tcctgtggat
2941 gtcaatattc tagctaagtg taaccccctgc ctatcaaatc cgtgtaaaaa tgatgcaca
3001 tgtaatagtg atccagttga ctttaccga tgcacctgtc catatggttt caaggggcag
3061 gactgtgatg tcccaattca tgcctgcatc agtaacccat gtaaacatgg aggaacttgc
3121 cacttaaagg aaggagaaga agatggattc tggtgtattt gtgctgatgg atttgaagga
3181 gaaaattgtg aagtcaacgt tgatgattgt aagataatg actgtgaaaa taattctaca
3241 tgtgtcgatg gcattaataa ctacacatgc ctttgcccac tgagtatac aggtgagttg
3301 tgtgaggaga agctggactt ctgtgcccag gacctgaacc cctgccagca cgattcaaag
3361 tgcatcctaa ctccaaaggg attcaaatgt gactgcacac agggtacgt aggtgaacac
3421 tgcgacatcg attttgacga ctgccaagac aacaagtgta aaaacggagc ccactgcaca
3481 gatgcagtga acggctatac gtgcatatgc cccgaaggtt acagtggctt gttctgtgag
3541 ttttctccac ccatggtcct ccctcgtacc agccctgtg ataattttga ttgtcagaat
3601 ggagctcagt gtatcgtcag aataaatgag ccaatatgtc agtgtttgcc tggctatcag
3661 ggagaaaagt gtgaaaaatt ggttagtgtg aattttataa acaaagagtc ttatcttcag
3721 attccttcag ccaaggttcg gcctcagacg aacataacac ttcagattgc cacagatgaa
3781 gacagcggaa tcctcctgta taagggtgac aaagaccata tcgcggtaga actctatcgg
3841 gggcgtgttc gtgccagcta tgacaccggc tctcatccag cttctgccat ttacagtgtg
3901 gagacaatca atgatggaaa cttccacatt gtggaactac ttgccttgga tcagagtctc
3961 tctttgtccg tggatggtgg aacccccaaa atcatcacta acttgtcaaa gcagtccact
4021 ctgaatttg actctccact ctatgtagga ggcatgccag ggaagagtaa cgtggcatct
4081 ctgcgccagg cccctgggca gaacggaacc agcttccacg gctgcatccg gaacctttac
4141 atcaacagtg agctgcagga cttccagaag gtgccgatgc aaacaggcat tttgcctggc
4201 tgtgagccat gccacaagaa ggtgtgtgcc catggcacat gccagcccag cagccaggca
4261 ggcttcacct gcgagtgcca ggaaggatgg atgggcccc tctgtgacca acggaccaat
4321 gaccccttgcc ttggaaataa atgcgtacat ggcacctgct tgcccatcaa tgcgttctcc
```

Figure 6 (CONT)

```
4381 tacagctgta agtgcttgga gggccatgga ggtgtcctct gtgatgaaga ggaggatctg
4441 tttaacccat gccaggcgat caagtgcaag cacgggaagt gcaggctttc aggtctgggg
4501 cagccctact gtgaatgcag cagtggatac acgggggaca gctgtgatcg agaaatctct
4561 tgtcgagggg aaaggataag agattattac caaaagcagc agggctatgc tgcttgccaa
4621 acaaccaaga aggtgtcccg attagagtgc agaggtgggt gtgcaggagg gcagtgctgt
4681 ggaccgctga ggagcaagcg gcggaaatac tctttcgaat gcactgacgg ctcctccttt
4741 gtggacgagg ttgagaaagt ggtgaagtgc ggctgtacga ggtgtgtgtc ctaaacacac
4801 tcccggcagc tctgtctttg gaaaaggttg tatacttctt gaccatgtgg gactaatgaa
4861 tgcttcatag tggaaatatt tgaaatatat tgtaaaatac agaacagact tatttttatt
4921 atgagaataa agactttttt tctgcatttg
```

SLIT2 UNDEREXPRESSION IN METASTATIC PROSTATE CANCER

CROSS REFERENCE TO RELATED APPLICATIONS

This application claims priority to provisional patent application Ser. No. 61/029,636, filed Feb. 19, 2008, which is herein incorporated by reference in its entirety.

STATEMENT REGARDING FEDERAL SPONSORSHIP

This invention was made with government support under CA097063 awarded by the National Institutes of Health and W81XWH-07-1-0107 awarded by the Army Medical Research and Materiel Command. The government has certain rights in the invention.

FIELD OF THE INVENTION

The present invention relates to compositions and methods for cancer diagnosis, research and therapy, including but not limited to, cancer markers. In particular, embodiments of the present invention relate to SLIT2 cancer markers that are useful as diagnostic markers and clinical and research targets for prostate cancer.

BACKGROUND OF THE INVENTION

Afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]).

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals. The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., J. Natl. Cancer Inst., 91:1033 [1999]; Maattanen et al., Br. J. Cancer 79:1210 [1999]; Schroder et al., J. Natl. Cancer Inst., 90:1817 [1998]). A major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., JAMA 274:1445 [1995]). This has resulted in a surge of equivocal prostate needle biopsies (Epstein and Potter J. Urol., 166:402 [2001]). Thus, development of additional serum and tissue biomarkers to supplement PSA screening is needed.

SUMMARY OF THE INVENTION

The present invention relates to compositions and methods for cancer diagnosis, research and therapy, including but not limited to, cancer markers. In particular, embodiments of the present invention relate to SLIT2 cancer markers that are useful as diagnostic markers and clinical and research targets for prostate cancer.

For example, in some embodiments, the present invention provides a method of determining a likelihood of survival in a subject diagnosed with cancer (e.g., prostate cancer), comprising: detecting the presence or absence of underexpression of SLIT2 in a sample from the subject. In some embodiments, underexpression of SLIT2 is indicative of a decreased probability of survival in the subject compared to a subject not having SLIT2 underexpression. In some embodiments, the sample is a tumor sample, a cell sample, a blood sample, a serum sample, or a urine sample. In some embodiments, detecting underexpression of SLIT2 comprises detecting underexpression of SLIT2 mRNA (e.g., by performing a detection technique selected from a hybridization assay or an amplification assay). In some embodiments, the amplification assay comprises a quantitative PCR assay. In some embodiments, detecting underexpression of SLIT2 comprises detecting underexpression of SLIT2 polypeptide (e.g., using an immunoassay).

The present invention further provides a method of determining gene expression associated with metastatic prostate cancer, comprising: detecting the presence or absence of underexpression of SLIT2 in a sample from a subject. In some embodiments, underexpression of SLIT2 is indicative of metastatic prostate cancer in the subject. In some embodiments, a finding of underexpression of SLIT2 is following by one or more of: additional diagnostic testing, treatment, watchful waiting, etc.

The present invention additionally provides a method of screening compounds, comprising contacting a cell (e.g., a cancer cell) underexpressing SLIT2 with a test compound and assaying the level of expression of SLIT2 in the presence of the test compound. In some embodiments, contacting the cell expressing SLIT2 with the test compound results in an increase in expression of SLIT2. In some embodiments, the cell is in vitro, ex vivo, or in vivo. In some embodiments, the cell is in a non-human animal. In some embodiments, the non-human animal has cancer.

DESCRIPTION OF THE FIGURES

FIG. 6 shows SLIT2 mRNA sequence (SEQ ID NO:1).

DEFINITIONS

Figure 1:
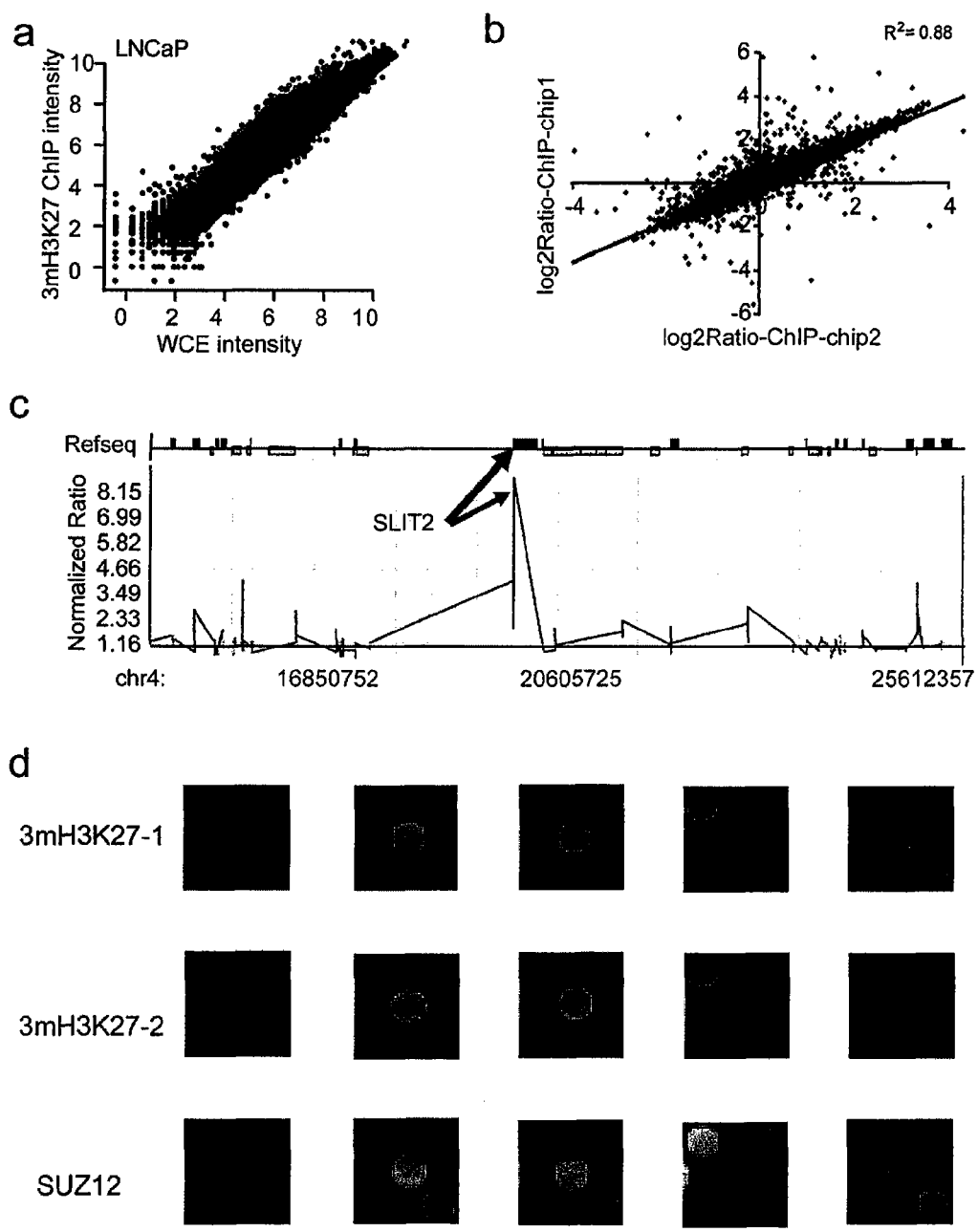
FIG. 1 shows that genome-wide location analyses of PRC2 and 3mH3K27 reveal SLIT2 as a direct target. (a) ChIP-on-chip was performed using ChIP-enriched chromatin by an anti-3mH3K27 antibody in LNCaP prostate cancer cells comparing to control whole cell extract (WCE) DNA. (b) Replicate ChIP-on-chip of 3mH3K27 show high correlation. (c) Chromosomal view of 3mH3K27 signal near SLIT2 promoter by ChIP-on-chip experiment. (d) Images of hybridized arrays showing five probes representing the proximal promoters of SLIT2 in 2 replicate ChIP-on-chip analyses of 3mH3K27 and one ChIP-on-chip of SUZ12.

To facilitate an understanding of this disclosure, terms are defined below:

As used herein, the term "underexpression of SLIT2" refers to a lower level of expression of SLIT2 nucleic acid (e.g., mRNA or genomic DNA) or protein relative to the level normally found. In some embodiments, expression is decreased at least 10%, preferably at least 20%, even more preferably at least 50%, yet more preferably at least 75%, still more preferably at least 90%, and most preferably at least 100% relative the level of expression normally found (e.g., in non-cancerous tissue). In some embodiments, normal expression levels are a population average (e.g., of subjects not diagnosed with cancer, age matched subjects not diagnosed with cancer, or ethnically matched subjects not diagnosed with cancer). In other embodiments, normal expression levels are levels of a given patient prior to diagnosis or early in the progression of disease. In some embodiments, a predetermined expression level cutoff (e.g., relative % or set level) is determined as the level that defines "underexpression of SLIT2). In some embodiments, cutoff levels for underexpression are determined experimentally based on research or diagnostic data. Expression levels may be determined using any suitable method, including, but not limited to, those disclosed herein.

As used herein, the terms "detect", "detecting", or "detection" may describe either the general act of discovering or discerning or the specific observation of a detectably labeled composition.

The term "RNA interference" or "RNAi" refers to the silencing or decreasing of gene expression by siNAs (e.g., "short interfering RNA", "siRNA", "short interfering nucleic acid molecule", "short interfering oligonucleotide molecule", or "chemically-modified short interfering nucleic acid molecule"). It is the process of sequence-specific, post-transcriptional gene silencing in animals and plants, initiated by siNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner (see, e.g., Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). In some embodiments, the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see, e.g., Martinez et al., 2002, Cell., 110, 563-574 and Schwarz et al., 2002, Molecular Cell, 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic intercations, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. In some embodiments, siNA molecules do not require the presence of nucleotides having a 2'-hydroxy group for mediating RNAi and as such, short interfering nucleic acid molecules of the invention optionally do not include any ribonucleotides (e.g., nucleotides having a 2'-OH group).

Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, e.g., Allshire, 2002, Science, 297, 1818-1819; Volpe et al, 2002, Science, 297, 1833-1837; Jenuwein, 2002, Science, 297, 2215-2218; and Hall et al., 2002, Science, 297, 2232-2237).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin siNA molecule of the invention can comprise an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex siNA molecule of the invention can comprise an antisense region having length sufficient to mediate RNAi in a cell or in vitro system (e.g. about 19 to about 22 nucleotides) and a sense region having about 3 to about 18 nucleotides that are complementary to the antisense region.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", with respect to RNA interference, it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siRNA) of the invention. In one embodiment, inhibition, down-regulation or reduction with an siRNA molecule is below that level observed in the presence of an inactive or attenuated molecule. In another embodiment, inhibition, down-regulation, or reduction with siRNA molecules is below that level observed in the presence of, for example, an siRNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "target gene" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts.

By "sense region" is meant a nucleotide sequence of a siRNA molecule having complementarity to an antisense region of the siRNA molecule. In addition, the sense region of a siRNA molecule can comprise a nucleic acid sequence having homology with a target nucleic acid sequence.

By "antisense region" is meant a nucleotide sequence of a siRNA molecule having complementarity to a target nucleic acid sequence. In addition, the antisense region of a siRNA molecule can optionally comprise a nucleic acid sequence having complementarity to a sense region of the siRNA molecule.

By "target nucleic acid" is meant any nucleic acid sequence whose expression or activity is to be modulated or detected. The target nucleic acid can be DNA or RNA, such as endogenous DNA or RNA, viral DNA or viral RNA, or other RNA encoded by a gene, virus, bacteria, fungus, mammal, or plant.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxymethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnosis, research and therapy, including but not limited to, cancer markers. In particular, embodiments of the present invention relate to SLIT2 cancer markers that are useful as diagnostic markers and clinical and research targets for prostate cancer.

EZH2 (Enhancer of Zest 2) has previously been identified as being up-regulated in aggressive prostate cancer. The Polycomb group (PcG) proteins are transcriptional repressors important for preserving cellular identity (Ringrose and Paro, Annu Rev Genet. 2004; 38:413-43 [2004]) and maintaining pluripotency and plasticity of embryonic stem cells (Boyer et al., 2006; Lee et al., 2006). They function in multi-protein Polycomb Repressive Complexes (PRCs), one of which is PRC2 (Levine et al., 2002). PRC2 includes SUZ12 (Suppressor of Zeste 12), EED (Embryonic Ectoderm Development) and EZH2 (Enhancer of Zeste 2), and is essential for the initial binding to target gene promoters (Rastelli et al., 1993). EZH2 is a histone methyltransferase (HMTase) that specifically methylates lysine 27 of histone H3 (H3K27), thus leading to target gene silencing (Cao et al., 2002; Kirmizis et al., 2004; Kuzmichev et al., 2002).

Experiments conducted during the course of development of embodiments of the present invention identified downstream targets of EZH2 that convey EZH2's function in prostate cancer progression. ChIP-on-chip (genome-wide location analysis) of EZH2 and H3K27 trimethylation (3mH3K27) on whole-genome promoters in the LNCaP prostate cancer cell line was performed. Experiments identified the tumor suppressor gene SLIT2 as a direct target of EZH2. In addition, the repressed expression of SLIT2 in localized prostate cancer was found to be associated with poor prognosis.

In Drosophila embryogenesis, the 'slit' gene has been shown to play a critical role in central nervous system midline formation. Itoh et al. (1998) cloned the SLIT2 gene, a human homolog of the Drosophila 'slit' gene. They also cloned 2 additional human 'slit' homologs, which they termed SLIT1 and SLIT3, as well as the rat homolog, Slit1. Each SLIT gene encodes a putative secreted protein, which contains conserved protein-protein interaction domains including leucine-rich repeats and epidermal growth factor-like (see 131530) motifs, similar to those of the Drosophila protein. The SLIT2 cDNA encodes a 1,529-amino acid polypeptide with 44.3% similarity to the Drosophila 'slit' protein. Northern blot analysis revealed that the human SLIT2 gene was expressed as an approximately 8.5-kb transcript primarily in the spinal cord. SLIT1 and SLIT3 mRNAs were primarily expressed in the brain and thyroid, respectively. In situ hybridization studies indicated that the rat Slit1 mRNA was specifically expressed in the neurons of fetal and adult forebrains. These data indicated that the SLIT genes form an evolutionarily conserved group in vertebrates and invertebrates, and that the mammalian SLIT proteins participate in the formation and maintenance of the nervous and endocrine systems by protein-protein interactions.

By fluorescence in situ hybridization, Georgas et al. (Cytogenet. Cell Genet. 86: 246-247, 1999) mapped the human SLIT2 gene to chromosome 4p15.2. The nucleotide sequence of human SLIT2 is described by accession number NM_004787 (SEQ ID NO:1; FIG. 6).

I. Diagnostic Applications

In some embodiments, the present invention provides methods of diagnosing and/or characterizing prostate cancer based on the presence or absence of underexpression of SLIT2. The disclosed underexpression of SLIT2 provides RNA and protein based diagnostic methods that detect, either directly or indirectly, the underexpression of SLIT2 mRNA or protein. The disclosed SLIT2 underexpression also provides compositions useful for diagnostic purposes, such as oligonucleotide probes that specifically detect the underexpression of SLIT2. Such compositions may be in the form of a kit.

The disclosed diagnostic methods may be qualitative or quantitative. Quantitative methods may, for example, discriminate between the presence or absence of cancer or between indolent and aggressive (e.g., metastatic) cancers via a cutoff or threshold level where expression above that level provides information on the aggressiveness of the cancer which provides useful diagnostic and/or prognostic (e.g., probability of survival) information to a treating physician or patient. Qualitative or quantitative diagnostic methods may include amplification of a target, such as by using a universal primer that amplifies a sequence that serves as an indicator for the presence or level of SLIT2.

The disclosed underexpression of SLIT2 may be detected along with other markers in a multiplex or panel format. Markers are selected for their predictive value alone or in combination with the underexpression of SLIT2. Exemplary prostate cancer markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); and, those disclosed in U.S. Pat. Nos. 5,854,206, 6,034,218, and 7,229,774 and U.S. Publication Nos. 20030175736 and 20070212702, each of which is herein incorporated by reference in its entirety. Markers for other cancers, diseases, infections, and metabolic conditions are also contemplated for inclusion in a multiplex or panel format.

The diagnostic methods as disclosed herein may be modified with reference to data correlating underexpression of SLIT2 with the presence, stage, aggressiveness or progression of the disease or the presence or risk of metastasis. The information provided by these diagnostic methods provide useful information to a physician who, based on that information, may choose an appropriate therapeutic treatment or other intervention for a particular patient.

A. Sample

Any biological sample suspected of containing underexpression of SLIT2 may be tested according to the disclosed methods. Such a sample may be tissue (e.g., prostate biopsy sample or tissue obtained by prostatectomy), blood, urine, semen, prostatic secretions or a fraction thereof (e.g., plasma, serum, urine supernatant, urine cell pellet or prostate cells), which may be obtained from a patient or other source of biological material, e.g., autopsy sample or forensic material. In preferred embodiments, a urine sample is collected immediately following an attentive digital rectal examination (DRE), which causes prostate cells from the prostate gland to shed into the urinary tract.

The sample may be processed to isolate or enrich the sample for SLIT2 protein or nucleic acid or cells whose expression of SLIT2 is of interest. A variety of known techniques that use standard laboratory practices may be used for this purpose, such as, e.g., centrifugation, immunocapture, cell lysis, and nucleic acid target capture (See, e.g., EP Pat. No. 1 409 727, herein incorporated by reference in its entirety).

B. RNA Detection

The disclosed underexpression of SLIT2 may be detected by detecting the level of SLIT2 mRNA using a variety of well known nucleic acid techniques that rely on standard laboratory methods, such as, e.g., nucleic acid sequencing, nucleic acid hybridization, and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as it is scanned from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 FISH

In some embodiments, underexpression of SLIT2 is detected using fluorescence in situ hybridization (FISH). The preferred FISH assays use bacterial artificial chromosomes (BACs), which have been used extensively in the human genome sequencing project (see *Nature* 409: 953-958 (2001)) and clones containing specific BACs are widely available or can be made by using standard laboratory practices. Each BAC clone from the human genome has been given a reference name that unambiguously identifies it. These names can be used to find a corresponding GenBank sequence and to order copies of the clone from a distributor.

Probes are generally labeled with appropriate fluorescent or other markers and then used in hybridizations. Specific protocols are well known in the art and can be readily adapted for detecting SLIT2 underexpression. Guidance regarding such methodology is provided in many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). Patents providing guidance on such methodology include U.S. Pat. Nos. 5,225,326; 5,545,524; 6,121,489 and 6,573,043, and commercially available kits also provide protocols for performing FISH (e.+g., from Oncor, Inc., Gaithersburg, Md.). All of these references are hereby incorporated by reference in their entirety and may be used along with similar references in the art to establish procedural steps convenient for a particular laboratory.

2.2 Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

3. Amplification

SLIT2 mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) typically require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800, 159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

4. Detection Methods

Non-amplified or amplified underexpression or expression of SLIT2 can be detected by any conventional means. For example, SLIT2 mRNA can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/ quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and many types of interacting label pairs are known (e.g., U.S. Pat. No. 6,534,274, herein incorporated by reference in its entirety).

Another example of a detection probe having self-complementarity is a "molecular beacon" (see U.S. Pat. Nos. 5,925, 517 and 6,150,097, herein incorporated by reference in entirety). Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS).

Other self-hybridizing probes are well known to those of ordinary skill in the art. By way of non-limiting example, probe binding pairs having interacting labels (e.g., see U.S. Pat. No. 5,928,862, herein incorporated by reference in its entirety) may be adapted for use in the compositions and methods disclosed herein. Probe systems used to detect single nucleotide polymorphisms (SNPs) might also be used. Additional detection systems include "molecular switches," (e.g., see U.S. Publ. No. 20050042638, herein incorporated by reference in its entirety). Other probes, such as those comprising intercalating dyes and/or fluorochromes, are also useful for detection of amplification products in the methods disclosed herein (e.g., see U.S. Pat. No. 5,814,447, herein incorporated by reference in its entirety).

C. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

Any method may be used that is capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

D. In Vivo Imaging

The underexpression of SLIT2 disclosed herein may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the disclosed cancer markers are described above.

The in vivo imaging methods that use the compositions disclosed herein that detect SLIT2 underexpression or products derived from them are useful in the diagnosis of cancers, particularly prostate cancer, that express the cancer markers disclosed herein. In vivo imaging visualizes the presence of a marker indicative of the cancer, allowing diagnosis and/or prognosis without the use of an unpleasant biopsy. For example, the presence of a marker indicative of cancers likely to metastasize can be detected. The in vivo imaging methods can further be used to detect metastatic cancers in other parts of the body.

In some embodiments, reagents (e.g., antibodies) specific for the cancer markers (e.g., SLIT2) are fluorescently labeled. The labeled antibodies are introduced into a subject (e.g., orally or parenterally). Fluorescently labeled antibodies are detected using any suitable method or system (e.g., see U.S. Pat. No. 6,198,107, herein incorporated by reference).

In some embodiments, antibodies are radioactively labeled. The use of antibodies for in vivo diagnosis is well known in the art, e.g., by using an antibody-based labeling system to image tumors (see Sumerdon et al., Nucl. Med. Biol 17:247-254 [1990], Griffin et al., J. Clin. Onc. 9:631-640 [1991], and Lauffer, Magnetic Resonance in Medicine 22:339-342 [1991]). The label used with an antibody-based system will depend on the imaging modality chosen, for example, radioactive labels such as Indium-111, Technetium-99m, or Iodine-131 for use with planar scans or single photon emission computed tomography (SPECT), positron emitting labels such as Fluorine-19 for use with positron emission tomography (PET), and paramagnetic ions such as Gadolinium (III) or Manganese (II) for use with MRI.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m is known (e.g., see Crockford et al., U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker, to insure that the antigen binding site on the antibody is protected. The antigen is separated after labeling.

In still further embodiments, in vivo biophotonic imaging (Xenogen, Almeda, Calif.) is used for in vivo imaging. This real-time in vivo imaging utilizes luciferase, an enzyme that catalyzes a light-emitting reaction. The luciferase gene is incorporated into cells, microorganisms, and animals (e.g., to produce a fusion protein with a cancer marker associated with SLIT2 underexpression) so that when the cancer marker is active a light emission occurs which is captured as an image and analyzed by using a CCD camera and appropriate software.

E. Compositions & Kits

Compositions for use in the disclosed diagnostic methods include, but are not limited to, probes, amplification oligonucleotides, and antibodies. In some embodiments, the compositions detect a product only when underexpression of SLIT2 is present. These compositions include, but are not limited to: a single labeled probe comprising a sequence that hybridizes to SLIT2 and can be quantitated and a pair of amplification oligonucleotides for quantitative PCR detection of SLIT2 underexpression, and an antibody for detection of the underexpression of SLIT2 polypeptide.

Any of these compositions, alone or in combination with other compositions disclosed herein or well known in the art, may be provided in the form of a kit. For example, the single labeled probe and pair of amplification oligonucleotides may be provided in a kit for the amplification and detection of SLIT2 underexpression. Kits may further comprise appropriate controls and/or detection reagents. Any one or more reagents that are useful, necessary, or sufficient in any of the methods described herein may be provided in the kit.

The probe and antibody compositions may also be provided in the form of an array.

II. Antibodies

SLIT2 polypeptides, which include fragments, derivatives and analogs thereof, which may be used as immunogens to produce antibodies useful for diagnostic and therapeutic applications. Such antibodies may be polyclonal or monoclonal, chimeric, humanized, single chain or Fab fragments, which may be labeled or unlabeled, all of which may be produced by using well known procedures and standard laboratory practices. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975).

In some embodiments, commercially available anti-SLIT2 antibodies are utilized (e.g., available from Santa Cruz Biotechnology, Inc (Santa Cruz, Calif.), Everest Biotech (Oxfordshire, UK), Novus Biologicals (Littleton, Colo.), ABR-Affinity BioReagents (Golden, Colo.), Lifespan Biosciences (Seattle, Wash.), Millipore Corporation (Billerica, Mass.), or Abcam (Cambridge, UK)).

IV. Drug Screening Applications

In some embodiments, the disclosed compositions and methods are used in drug screening assays (e.g., to screen for anticancer drugs). These screening methods use cancer markers that include those associated with SLIT2 underexpression. For example, an embodiment may screen for compounds that alter (e.g., increase) the expression of SLIT2 or associated signaling molecules (e.g., decrease expression or activity of upstream modulators of SLIT2). Compounds or agents to be screened for may interfere with transcription (e.g., by interacting with a promoter region), may interfere with mRNA produced from SLIT2 (e.g., by RNA interference, antisense technologies, etc. (See e.g., below discussion of design of nucleic acid based compounds)), or may interfere with pathways that are upstream or downstream of the biological activity of SLIT2. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression product associated with SLIT2 and inhibit or enhance its biological function.

In some embodiments, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

The test compounds can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem.

37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

VI. Therapeutic Applications

Some embodiments provide therapies for cancer (e.g., prostate cancer). Preferred therapy embodiments target SLIT2 directly or indirectly.

A. Antisense

In some embodiments, the methods involve, for example, the delivery of nucleic acid molecules targeting SLIT2 or SLIT2 pathway component expression and/or activity within cancer cells (e.g., prostate). For example, in some embodiments, the present invention employs compositions comprising oligomeric antisense compounds, particularly oligonucleotides, for use in modulating the function of nucleic acid molecules encoding SLIT2 upstream modulators (e.g., EZH2), ultimately modulating the amount of SLIT2 expressed. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of upstream modulators of SLIT2. In the context of the present invention, "modulation" means either an increase (stimulation) or a decrease (inhibition) in the expression of a gene. For example, expression may be inhibited to potentially prevent tumor growth, inhibition of complement mediated lysis, angiogenesis and proliferation associated with underexpression of SLIT2 (e.g., in prostate cancer).

B. shRNA

In some embodiments, the present invention provides shRNAs that inhibit the expression of SLIT2 upstream modulators (e.g., in prostate cancer cells). A short hairpin RNA (shRNA) is a sequence of RNA that makes a tight hairpin turn that can be used to silence gene expression via RNA interference. shRNA typically uses a vector introduced into cells and utilizes a promoter (e.g., the U6 promoter) to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

C. siRNA

In some embodiments, the present invention provides siRNAs that inhibit the expression of upstream modulators of SLIT2 (e.g., in prostate cancer cells). siRNAs are extraordinarily effective at lowering the amounts of targeted RNA (e.g., SLIT2 RNA), and by extension proteins, frequently to undetectable levels. The silencing effect can last several months, and is extraordinarily specific, because one nucleotide mismatch between the target RNA and the central region of the siRNA is frequently sufficient to prevent silencing (see, e.g., Brummelkamp et al, Science 2002; 296:550-3; and Holen et al, Nucleic Acids Res. 2002; 30:1757-66). An important factor in the design of siRNAs is the presence of accessible sites for siRNA binding. Bahoia et al., (J. Biol. Chem., 2003; 278: 15991-15997) describe the use of a type of DNA array called a scanning array to find accessible sites in mRNAs for designing effective siRNAs. These arrays comprise oligonucleotides ranging in size from monomers to a certain maximum, usually Comers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7 mers to 25 mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

D. Delivery of Nucleic Acids

Introduction of molecules carrying genetic information into cells is achieved by any of various methods including, but not limited to, directed injection of naked DNA constructs, bombardment with gold particles loaded with the constructs, macromolecule mediated gene transfer using, for example, liposomes, biopolymers, and the like, and ex vivo transfection and/or gene therapy followed by transplantation. The present invention is not limited to a particular approach for introducing molecules carrying genetic information to a subject (e.g., a human subject, a non-human subject). In some embodiments, the methods employ a nanovector delivery system (e.g., a cationic liposome-mediated gene transfer system; a lipoplex) for delivering gene therapeutics to a subject. Current approaches to deliver gene therapeutics to cancer patients often employ either viral or non-viral vector systems. Viral vector-directed methods show high gene transfer efficiency but are deficient in several areas. The limitations of a viral approach are related to their lack of tumor targeting and to residual viral elements that can be immunogenic, cytopathic, or recombinogenic. To circumvent these problems, progress has been made toward developing non-viral, pharmaceutical formulations of gene therapeutics for in vivo human therapy, particularly nanovector delivery systems (e.g., cationic liposome-mediated gene transfer systems). Indeed, there are multiple clinical trials underway using nanovector delivery systems for gene delivery, and liposomes for delivery of chemotherapeutics such as doxorubicin are already on the market for breast cancer chemotherapy. Features of nanovector delivery systems (e.g., cationic liposomes) that make them versatile and attractive include: ease of preparation, ability to complex large pieces of DNA/RNA, the ability to transfect many different types of cells, including non-dividing cells, and the lack of immunogenicity or biohazard activity.

In some embodiments, the nanovector delivery systems (e.g., cationic liposomes) are configured to bear a ligand recognized by a cell surface receptor (e.g., to increase desired targeting to, for example, a tumor). The nanovector delivery systems are not limited to a particular ligand recognized by a cell surface receptor. In some embodiments, the ligand is recognized by a cell surface receptor specific to a tumor. In some embodiments, the ligand is transferrin (Tf). In some embodiments, the ligand is a single chain antibody fragment (scFv) (e.g., specific to Tf). Receptor-mediated endocytosis represents a highly efficient internalization pathway in eukaryotic cells. The presence of a ligand on a nanovector delivery systems (e.g., cationic liposome; lipoplex) facilitates the entry of DNA into cells. Recently, a tumorspecific, ligand-targeting, self-assembled nanoparticle-DNA lipoplex system designed for systemic gene therapy of cancer was developed (see, e.g., U.S. Pat. No. 6,749,863; Tibbetts R S, Genes Dev 2000; 14:2989-3002; Zou L, Science 2003; 300: 1542-1548; each of which is herein incorporated by reference). These nanovector systems employ transferrin (Tf) or a single chain antibody fragment (scFv) against the transferrin receptor which is overexpressed in the majority of human cancers, including pancreatic cancer (see, e.g., Busino L, et al., Nature 2003; 426: 87-91). TfR-scFv-targeted nanovectors were recently approved by the FDA for clinical testing and the first Phase I clinical trial for non-viral systemic p53 gene therapy is ongoing.

Some methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is incorporated herein by reference in their entireties.

E. Antibodies

Some embodiments are or use antibodies and/or small molecules that target prostate tumors that underexpress SLIT2. In some embodiments, the therapeutic regimen is selected based on a diagnostic result and uses a suitable antibody (e.g., monoclonal, polyclonal, or synthetic) in the therapeutic methods. In preferred embodiments, the antibodies used for cancer therapy are humanized antibodies. Methods for humanizing antibodies are well known (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a SLIT pathway or upstream modulator, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of tumor cells. Embodiments may use any pharmacologic agent that can be conjugated to an antibody, and delivered in active form.

Exemplary anticellular agents include chemotherapeutic agents, radioisotopes, and cytotoxins. Such therapeutic antibodies may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, $\alpha$-sarcin, aspergillin, restrictocin, a ribonuclease, diphtheria toxin or pseudomonas exotoxin, to mention just a few examples. In some preferred embodiments, deglycosylated ricin A chain is used.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, some embodiments provide immunotoxins targeted against SLIT2 upstream modulators. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described herein. In preferred embodiments, administration of an antibody composition that targets a moiety associated with SLIT2 results in a measurable decrease in cancer (e.g., decrease or elimination of tumor).

F. Pharmaceutical Compositions

A therapeutic nucleic acid molecule of the present invention can be adapted for use to treat any disease, infection or condition associated with gene expression, and other indications that can respond to the level of gene product in a cell or tissue, alone or in combination with other therapies. For example, a therapeutic nucleic acid molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074), poly (lactic-co-glycolic)acid (PLGA) and PLCA microspheres (see for example U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262. Many examples in the art describe CNS delivery methods of oligonucleotides by osmotic pump, (see Chun et al., 1998, Neuroscience Letters, 257, 135-138, D'Aldin et al., 1998, Mol. Brain Research, 55, 151-164, Dryden et al., 1998, J. Endocrinol., 157, 169-175, Ghimikar et al., 1998, Neuroscience Letters, 247, 21-24) or direct infusion (Broaddus et al., 1997, Neurosurg. Focus, 3, article 4). Other routes of delivery include, but are not limited to oral (tablet or pill form) and/or intrathecal delivery (Gold, 1997, Neuroscience, 76, 1153-1158). More detailed descriptions of nucleic acid delivery and administration are provided in Sullivan et al., supra, Draper et al., PCT WO93/23569, Beigelman et al., PCT WO99/05094, and Klimuk et al., PCT WO99/04819 all of which have been incorporated by reference herein. The siNAs of the instant invention can be used as pharmaceutical agents. Pharmaceutical agents prevent, modulate the occurrence, or treat (alleviate a symptom to some extent, preferably all of the symptoms) of a disease state in a subject.

Thus, embodiments of the present invention feature a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes siRNA molecules to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant a composition or formulation that allows for the effective distribution of nucleic acid molecules in the physical location most suitable for their desired activity. Non-limiting examples of agents suitable for formulation with the nucleic acid molecules of embodiments of the instant invention include: P-glycoprotein inhibitors (such as Pluronic P85), which can enhance entry of drugs into the CNS (Jolliet-Riant and Tillement, 1999, Fundam. Clin. Pharmacol., 13, 16-26); biodegradable polymers, such as poly (DL-lactide-coglycolide) microspheres for sustained release delivery after intracerebral implantation (Emerich, D F et al, 1999, Cell Transplant, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies include, but are not limited to, material described in Boado et al., 1998, J. Pharm. Sci., 87, 1308-1315; Tyler et al., 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation based on their ability to avoid accumulation in metabolically aggressive MPS tissues such as the liver and spleen.

Embodiments of the present invention also include compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer. The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols. Nucleic acid molecules can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In some embodiments, the methods of the present invention directed toward increasing SLIT2 expression and/or activity, further involve co-administration with an anti-cancer agent (e.g., chemotherapeutic). The present invention is not limited by type of anti-cancer agent co-administered. Indeed, a variety of anti-cancer agents are contemplated to be useful in the present invention including, but not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate;

Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other anti-cancer agents include: Antiproliferative agents (e.g., Piritrexim Isothionate), Antiprostatic hypertrophy agent (e.g., Sitogluside), Benign prostatic hypertrophy therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Another category of anti-cancer agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2'deoxyadenosine; Fludarabine-$PO_4$; mitoxantrone; mitozolomide; Pentostatin; and Tomudex. One particularly preferred class of anticancer agents are taxanes (e.g., paclitaxel and docetaxel). Another important category of anticancer agent is annonaceous acetogenin. Other cancer therapies include hormonal manipulation. In some embodiments, the anti-cancer agent is tamoxifen or the aromatase inhibitor arimidex (i.e., anastrozole).

VII. Transgenic Animals

Embodiments include generation of transgenic animals comprising or lacking an exogenous cancer marker gene that is identical to or representative of SLIT2 as described herein, which includes mutants and variants thereof (e.g., truncations or single nucleotide polymorphisms). In preferred embodiments, the transgenic animal displays an altered phenotype (e.g., increased or decreased presence of markers associated with SLIT2) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

Such transgenic animals are useful in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal carry the incorporated transgene. This is reflected in the efficient transmission of the transgene to offspring of the founder since 50% of the germ cells harbor the transgene based on standard Mendelian genetics. Methods for making transgenics are well known (e.g., see U.S. Pat. No. 4,873,191, which is herein incorporated by reference in its entirety).

In other embodiments, retroviral infection is used to introduce transgenes into a non-human animal. In some embodiments, the retroviral vector is used to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are used to form an embryo. ES cells are obtained by culturing preimplantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is used to knock-out gene function or create deletion mutants (e.g., truncation mutants), using well known methods (see U.S. Pat. No. 5,614,396, incorporated herein by reference).

EXPERIMENTAL

The following examples are provided to demonstrate and illustrate certain preferred embodiments and aspects of the compositions and methods disclosed herein, but are not to be construed as limiting the scope of the claimed invention.

Example 1

SLIT2 Cancer Markers

This Example describes the characterization of SLIT2 expression in prostate cancer.

A. Materials and Methods

Cell Culture

LNCaP and DU145 prostate cancer cells were cultured in RPMI supplemented with 10% fetal bovine serum (Invitrogen, Carlsband, Calif.). RWPE cells were grown in Keratinocyte-Serum Free medium (Invitrogen) supplemented with 5 ng/ml human recombinant EGF and 0.05 mg/ml bovine pituitary extract. H16N2 immortalized human mammary epithelial cells were grown in Ham's F12 with supplements.

Chromatin Immunoprecipitation and Genome-Wide Location Analysis

ChIP was performed according to published protocols with slight modifications (Boyd et al., 1998). Briefly, formaldehyde was added directly to the cultured cells to a final concentration of 1%. For metastasis tissues, samples were first chopped into small pieces with a razor blade and transferred into 5-10 ml PBS before adding formaldehyde. Cells were rotated at room temperature for 10 min. The crosslinking was stopped by ½0V of 2.5M Glycine and the cells were washed with 1×PBS and harvested in 1×PBS with proteinase inhibitors. Metastasis tissue samples were further disaggregated using a tissue homogenizer. The cells were then pelleted and resuspended in cell lysis buffer containing protease inhibitors. After incubation in cell lysis buffer for 10 min, the samples were pelleted, resuspended in nuclei lysis buffer and sonicated to chromatins with an average size of 500 bp. The chromatins were precleared using Salmon sperm DNA/Protein A Agarose-50% slurry and incubated with specific antibodies overnight. Antibodies used in this study include EZH2 (BD Bioscience), EED (Upstate), SUZ12 (Abcam), trimethylated H3K27 (Upstate), Acetyl-H3K27 (Upstate), Myc (Abcam), and IgG control (Santa Cruz). The next day, the antibody-bound chromatin was pooled down using protein A/agarose, washed extensively, and reverse-crosslinked.

Immunoprecipitated DNA and whole cell extract DNA were purified by treatment with RNase A, proteinase K and purified using Qiaquick PCR purification kit (Qiagen, Valencia, Calif.). The purified DNA was used for PCR analysis of enrichment.

Purified DNA was blunted and ligated to linkers and amplified by a two-stage ligation-medated PCR (LM-PCR) protocol (Lee et al., 2006) to generate enough chromatins for PCR analysis of multiple target genes or for hybridization to promoter arrays. Equal amount of amplified input and ChIP-enriched chromatins were subjected to PCR testing for enrichment of target gene promoters.

A total of 200 ng of either whole cell extract DNA or immunoenriched DNA was labeled and purified using BioPrime array CGH genomic labeling kits (Invitrogen, Carlsbad, Calif.). Whole cell extract DNA was labeled with Cy3 dye whereas immunoenriched DNA was labeled with Cy5 dye (Perkin Elmer, Wellesley, Mass.). A total of 2.5 μg each of Cy3- or Cy5-labeled DNA were combined and hybridized at 65° C. for 40 hours to hu6k human proximal promoters (Aviva Systems Biology, San Diego, Calif.) containing a set of 4,839 well-annotated promoters of human genes with clearly defined functions (Li et al., 2003).

The hybridized promoter chips were scanned using the GenePix 4000B scanner (Axon, Foster City, Calif.) and analyzed with the GenePix Pro3.0 to extract intensity values and other quality-control parameters. Spot intensity was adjusted by subtraction of the background signal. Features of low intensity (<1000) and bad spots were flagged and excluded from further analysis. Non-flagged features with intensity of 1 standard deviation over background in both channels were included for normalization. The Cy5 and Cy3 channels were normalized by making the mean of the medians-of-Ratios of the normalization features to 1. For all non-flagged features, the normalized median of ratio was taken for further analysis.

B. Results

Slit2 Promoter is a Target of EZH2-Mediated H3K27 Tri-methylation in Prostate Cancer To investigate target genes of EZH2 in prostate cancer, genome-wide location analysis of 3mH3K27 in the LNCaP prostate cancer cell line was performed. Duplicate ChIP-on-chip analysis of 3mH3K27 demonstrated that this assay is highly reproducible and thus reliable in detecting binding targets. SLIT2 was one of the top target genes found occupied by EZH2-containing PRC2 complex proteins and the 3mH3K27 in multiple ChIP-on-chip assays (FIG. 1). This result indicates that SLIT2 is a target of EZH2-mediated transcriptional repression.

Slit2 Expression is Down-Regulated in Metastatic Prostate Cancer

Figure 2:
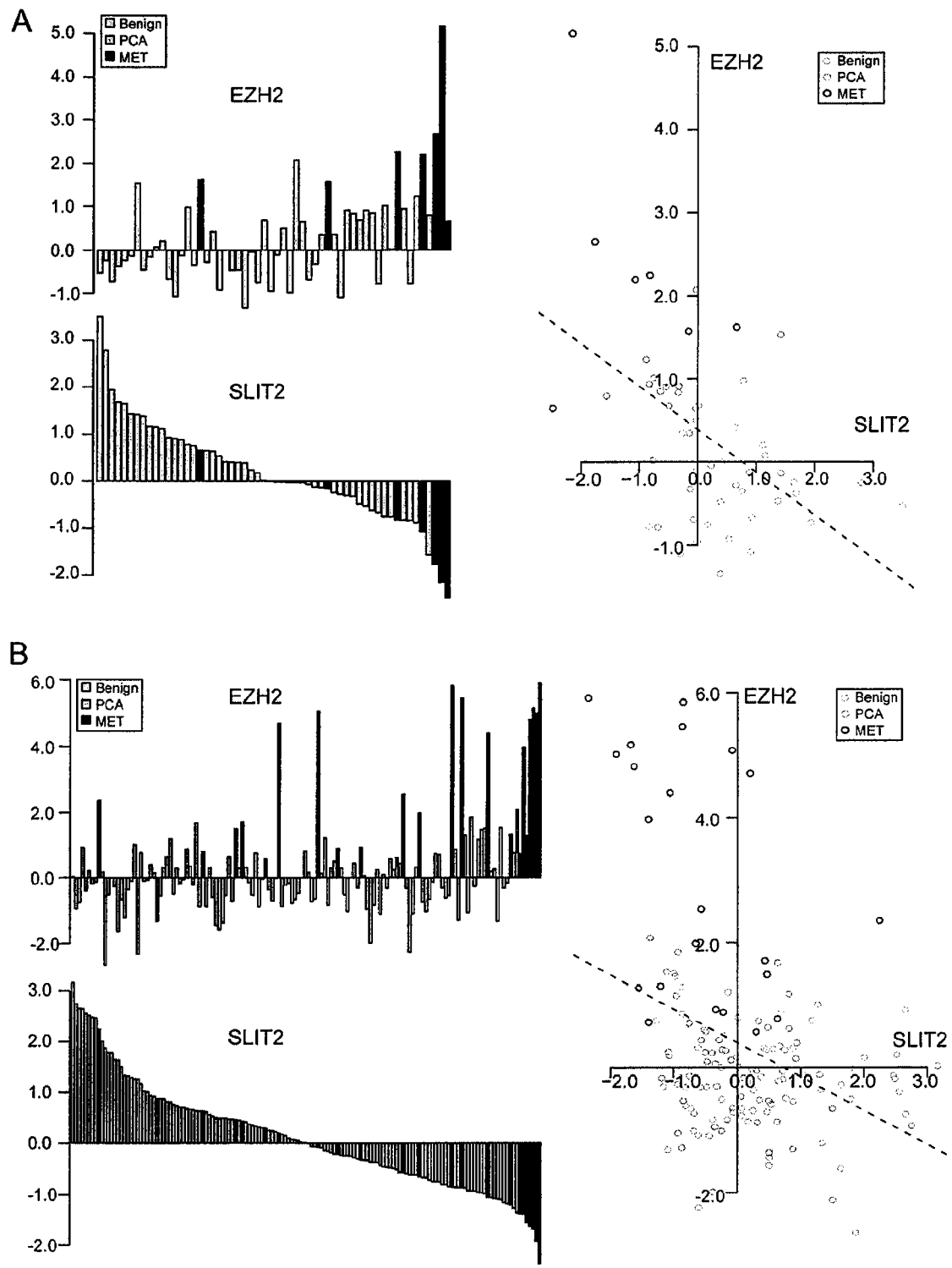
FIG. 2 shows a negative correlation between the transcript levels of EZH2 and SLIT2 in multiple prostate cancer gene expression datasets. (a) dataset of the present invention and (b) Yu et al. dataset [Yu, 2003].

To confirm that EZH2 represses SLIT2, previously published prostate cancer microarray profiling studies were examined. It was found that SLIT2 is significantly down-regulated in metastatic prostate cancer compared to benign or localized prostate cancer. There was a negative association between the expression levels of EZH2 and SLIT2 (FIG. 2). Furthermore, to confirm this high-throughput gene expression data, qRT-PCR analysis of EZH2 and SLIT2 in a panel of 8 benign prostate, 7 localized prostate cancer and 7 metastatic prostate cancer samples was performed. The results confirmed that SLIT2 is downregulated in metastatic prostate cancer and the expression level of SLIT2 is negatively associated with that of EZH2 (FIG. 3a).

Figure 3:
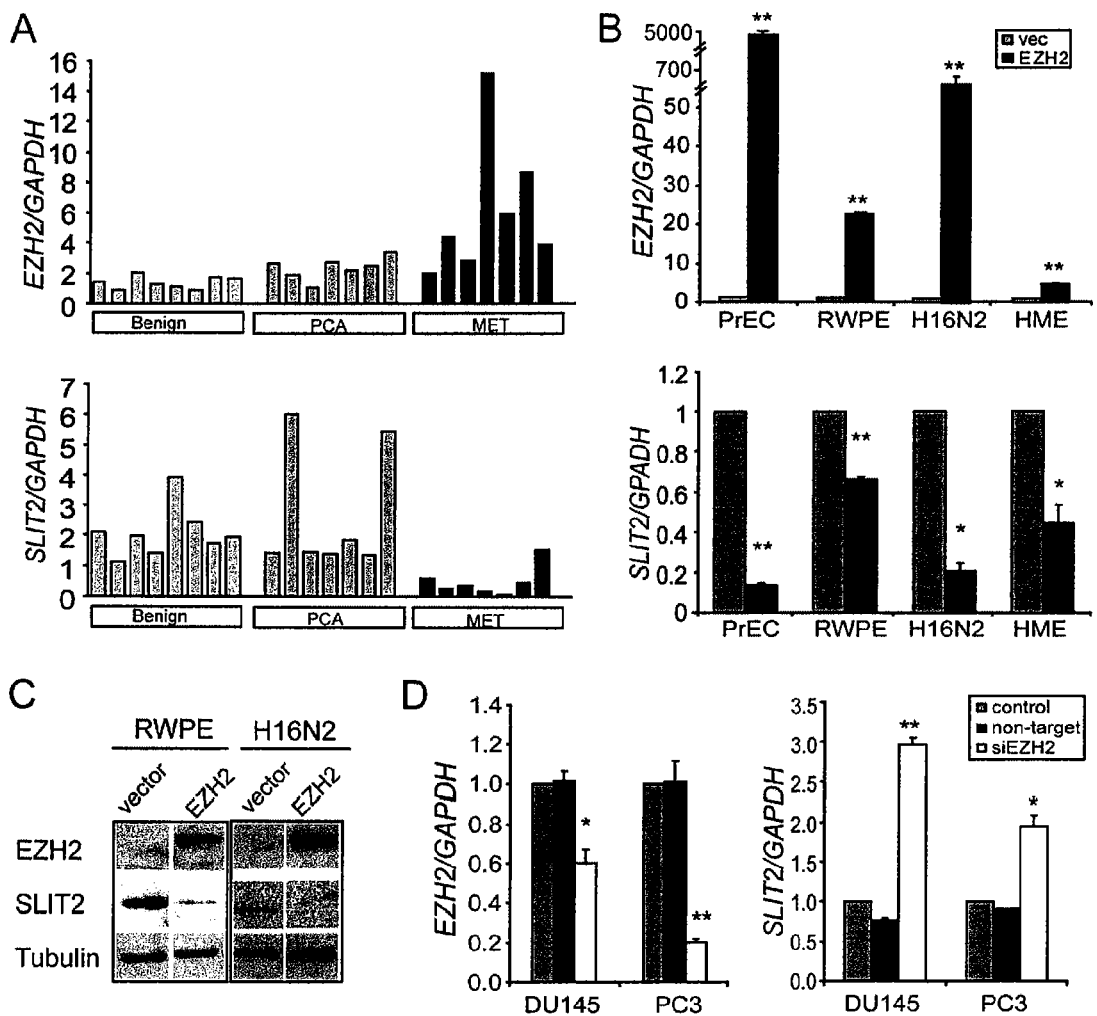
FIG. 3 shows that SLIT2 expression is negatively regulated by EZH2. (a) QRT-PCR analysis of EZH2 and SLIT2 transcripts in a cohort of 8 benign prostate hyperplasia (Benign), 7 localized prostate cancer (PCA), and 7 metastatic prostate cancer (MET) tissues. Expression of target genes was normalized to the amount of the GAPDH housekeeping gene. (b) EZH2 overexpression represses the transcript levels of SLIT2. (c) Immunoblot analysis of EZH2 and SLIT2 in benign immortalized prostate cell line (RWPE) and breast cell line (H16N2) following infection with EZH2 adenovirus or vector control for 48 hrs. (d) QRT-PCR analysis of EZH2 and SLIT2 transcripts in DU145 and PC3 prostate cancer cell lines following RNA interference of EZH2 or controls. Error bars represent mean±SEM. *$p<0.05$ and **$p<0.01$ by t-test.

Slit2 is Bound by the PRC2 Complex Proteins and Repressed by EZH2 Overexpression To recapitulate EZH2-mediated repression of SLIT2 in model systems, eZH2 expression was altered by either adenovirus overexpression or RNA interference of EZH2. Immunobloand qRT-PCR analysis demonstrated that SLIT2 expression is negatively regulated by EZH2 (FIG. 3).

Figure 4:
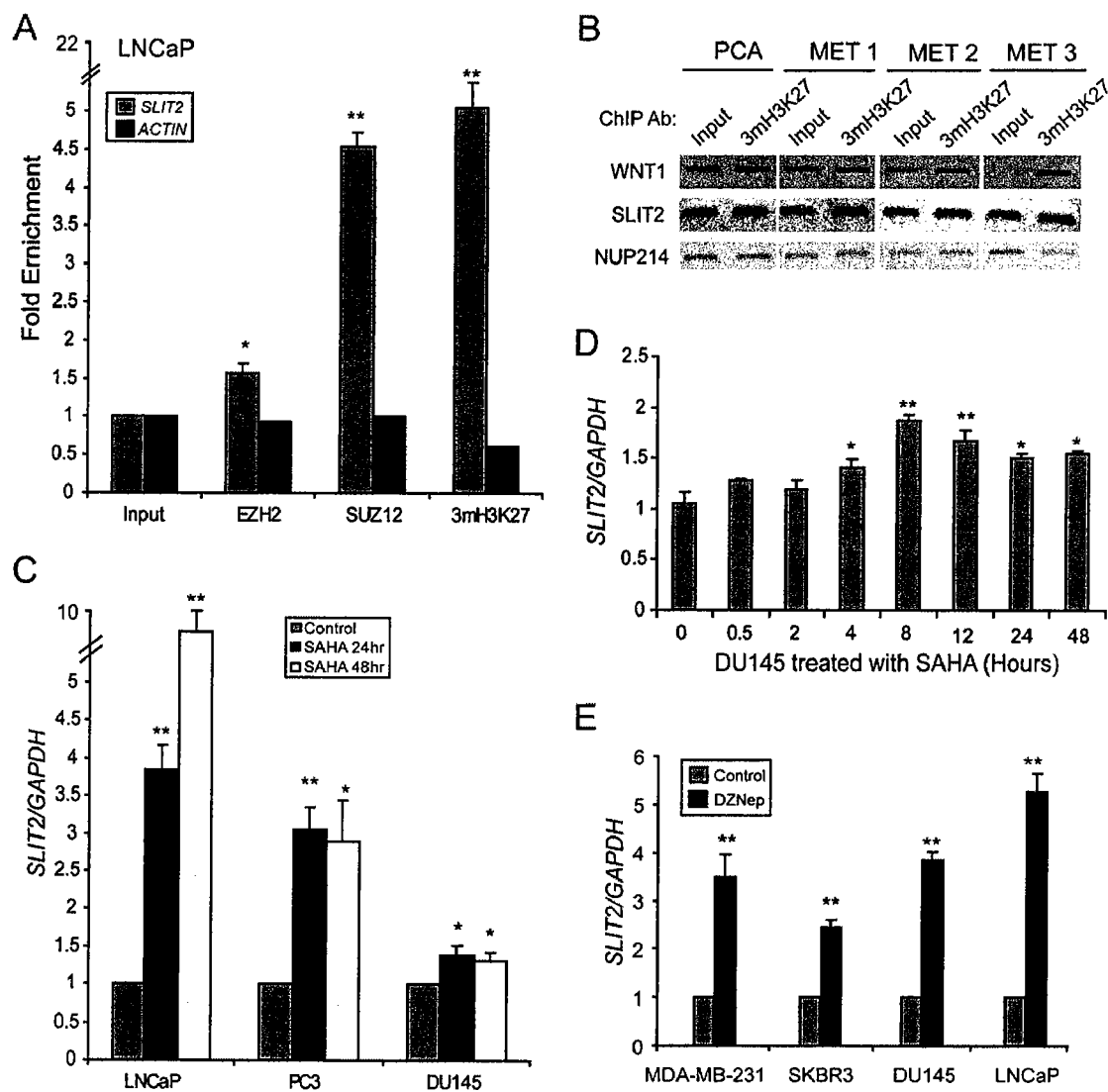
FIG. 4 shows that the SLIT2 promoter is directly regulated by EZH2 and H3K27 trimethylation. (a) The SLIT2 promoter is co-occupied by the PRC2 complex proteins and trimethylated at H3K27. (b) Localized prostate cancer and hormone refractor metastatic (MET) prostate cancer tissues were subjected to ChIP using anti-3mH3K27 antibody. (c) SLIT2 expression is up-regulated by a histone deacetylase (HDAC) inhibitor SAHA. (d) QRT-PCR analysis of SLIT2 in DU145 prostate cancer cell lines following a time-course treatment of 5 uM of SAHA. (e) Marked up-regulation of SLIT2 transcript by the PRC2-inhibiting compound DZNep. In panel c, d, e of this figure, expression of target genes was normalized to the amount of the GAPDH housekeeping gene. Error bars represent mean±SEM. *$p<0.05$ and **$p<0.01$ by t-test.

Furthermore Chromatin immunoprecipitation assay demonstrated that EZH2, SUZ12 and 3mH3K37 co-occupy the SLIT2 promoter in LNCaP prostate cancer cells and in metastatic prostate cancer tissues. The treatment of HDAC inhibitor (SAHA) or an EZH2-inhibiting compound was able to restore the expression level of SLIT2 (FIG. 4).

Low Level of SLIT2 Correlates with Poor Cancer Outcome

Figure 5:
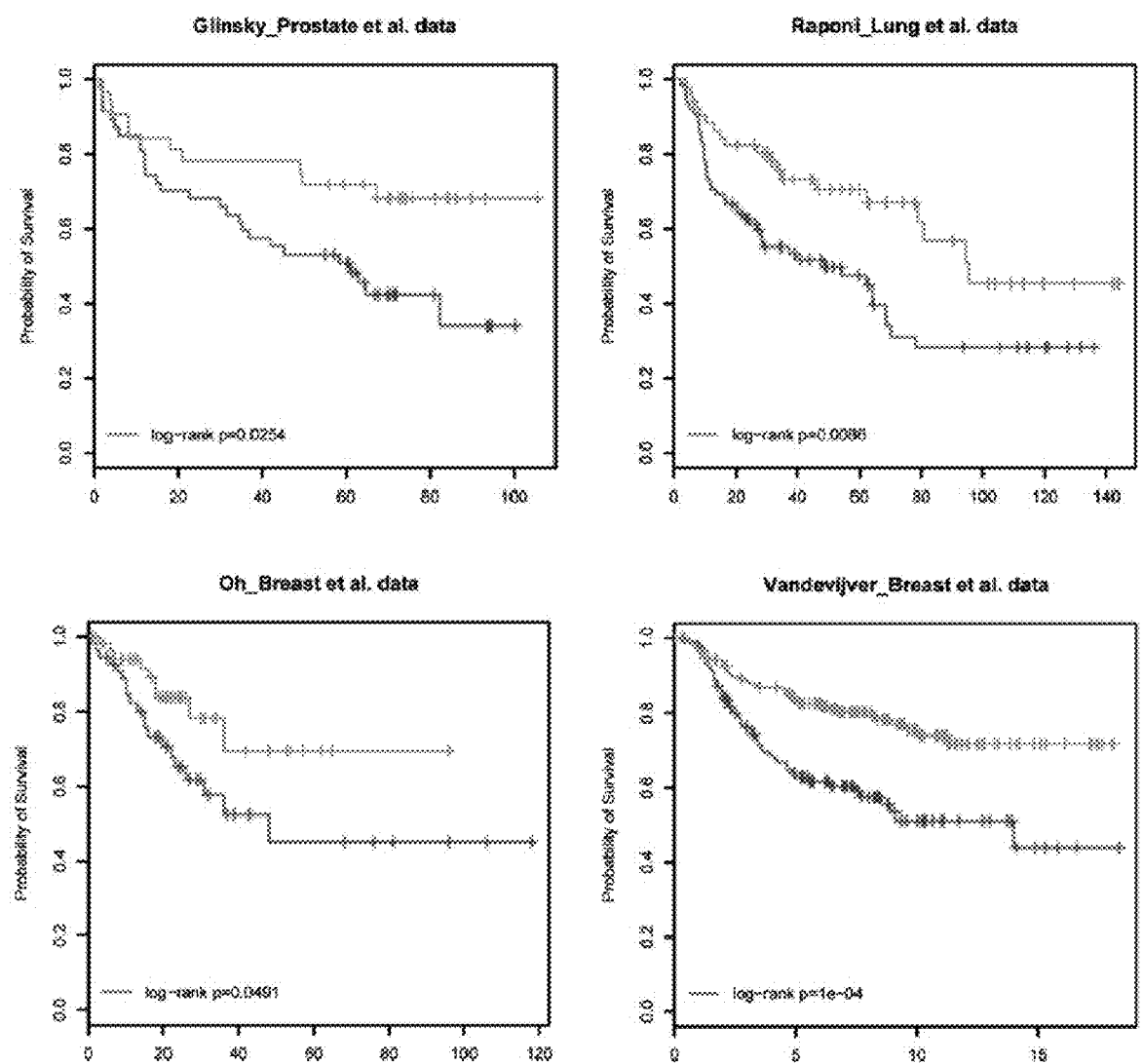
FIG. 5 shows that the expression level of SLIT2 predicts clinical outcome in multiple cancer microarray profiling datasets.
Figure 5:
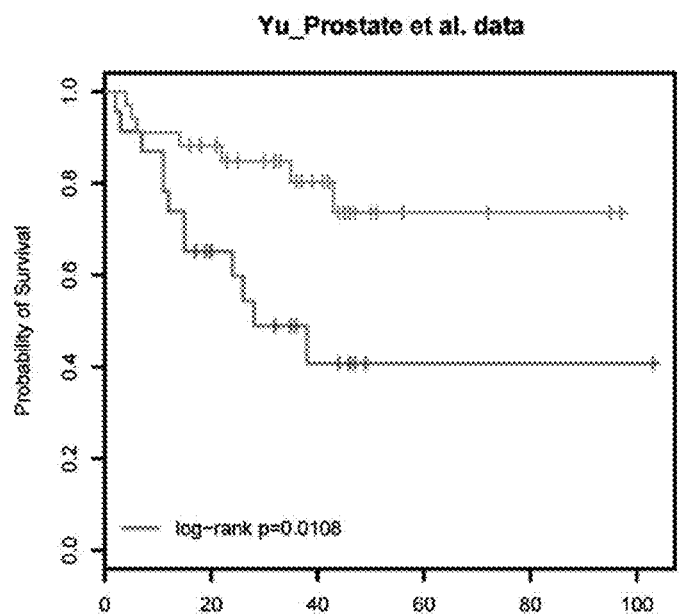
Figure 5:
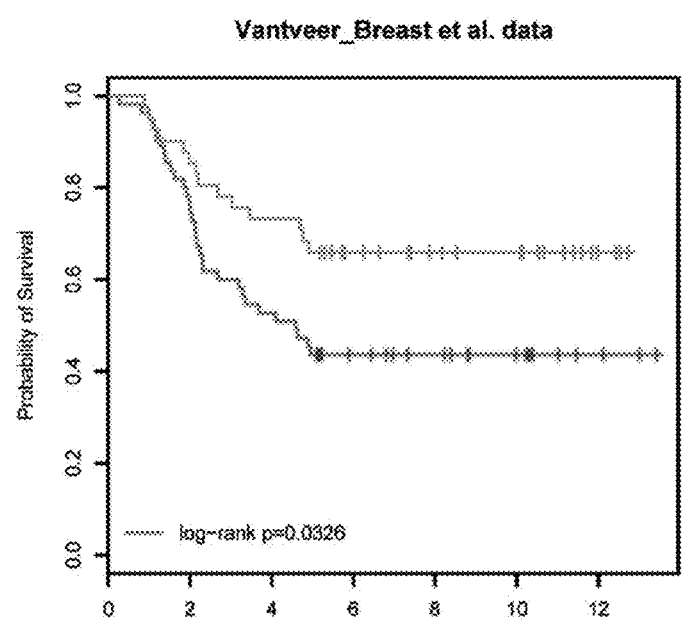
Figure 5:
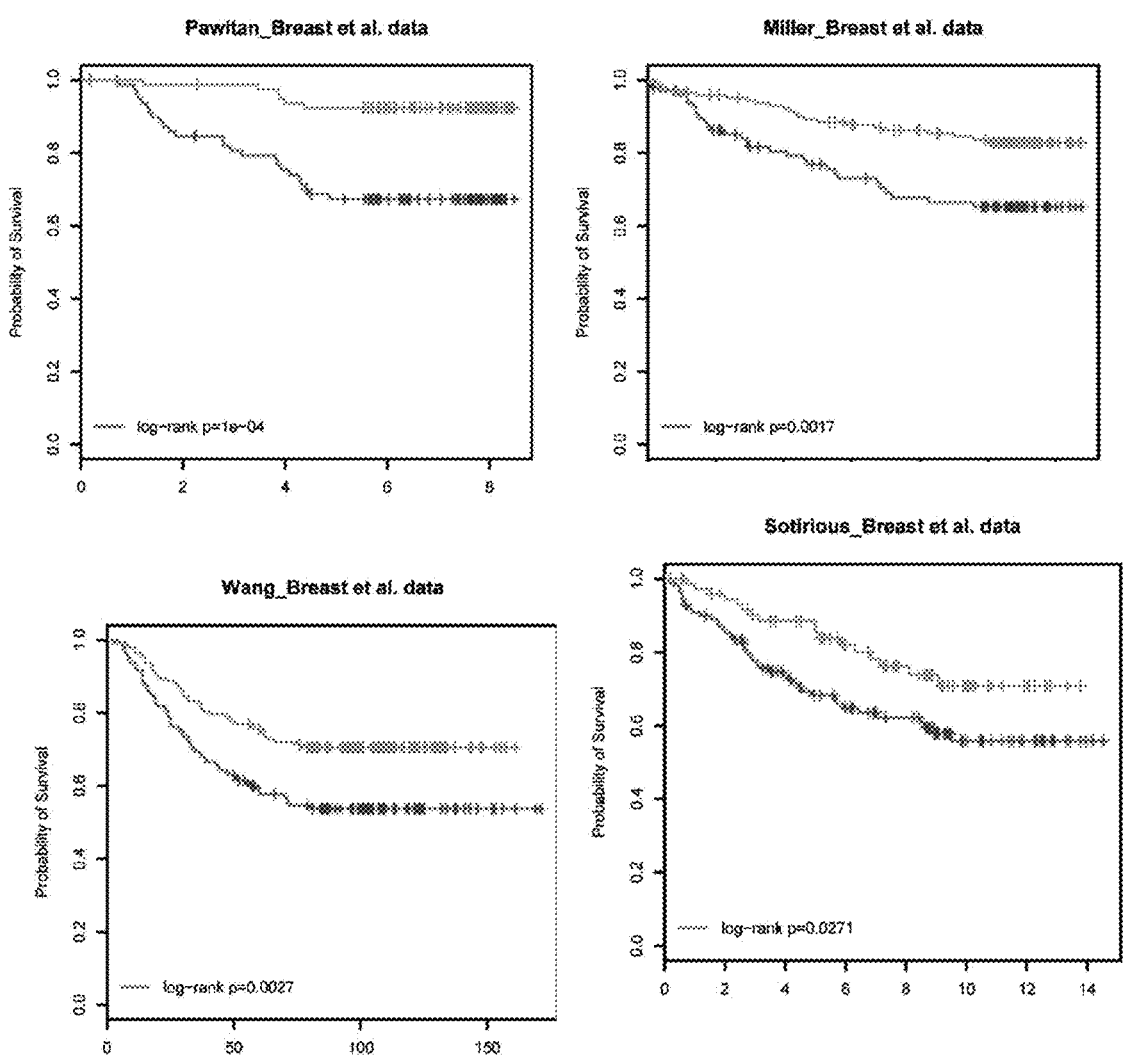

It was observed that SLIT2 functions as a prognostic biomarker of prostate cancer. In multiple cancer microarray profiling dataset, the expression level of SLIT2 is found to be associated with clinical outcome by Kaplan-Meier survival analysis (FIG. 5). Low expression level of SLIT2 is predictive of poor prognosis in multiple solid tumor types.

All publications, patents, patent applications and sequences identified by accession numbers mentioned in the above specification are herein incorporated by reference in their entirety. Although the invention has been described in connection with specific embodiments, it should be understood that the invention as claimed should not be unduly limited to such specific embodiments. Modifications and variations of the described compositions and methods of the invention that do not significantly change the functional features of the compositions and methods described herein are intended to be within the scope of the following claims.

We claim:

1. A method of diagnosing metastatic prostate cancer, comprising: a) detecting the presence or absence of underexpression of SLIT2 in a prostate cancer sample from a subject using an in vitro assay; and b) diagnosing metastatic prostate cancer in said subject when underexpression of SLIT2 is detected.

2. The method of claim 1, wherein said sample is selected from the group consisting of a tumor sample, a cell sample, a blood sample, a serum sample, and a urine sample.

3. The method of claim 1, wherein said detecting underexpression of SLIT2 comprises detecting underexpression of SLIT2 mRNA.

4. The method of claim 3, wherein said detecting underexpression of SLIT2 mRNA comprises performing a detection technique selected from the group consisting of hybridization assay, and an amplification assay.

5. The method of claim 4, wherein said amplification assay comprises a quantitative PCR assay.

6. The method of claim 1, wherein said detecting underexpression of SLIT2 comprises detecting underexpression of SLIT2 polypeptide.

7. The method of claim 6, wherein said detecting underexpression of SLIT2 polypeptide comprises an immunoassay.

* * * * *

SEQUENCE LISTING

```
<160> NUMBER OF SEQ ID NOS: 1

<210> SEQ ID NO 1
<211> LENGTH: 4950
<212> TYPE: DNA
<213> ORGANISM: Homo sapiens

<400> SEQUENCE: 1
cagagcaggg tggagagggc ggtgggaggc gtgtgcctga gtgggctcta ctgccttgtt      60
ccatattatt ttgtgcacat tttccctggc actctgggtt gctagccccg ccgggcactg     120
ggcctcagac actgcgcggt tccctcggag cagcaagcta aagaaagccc ccagtgccgg     180
cgaggaagga ggcggcgggg aaagatgcgc ggcgttggct ggcagatgct gtccctgtcg     240
ctggggttag tgctggcgat cctgaacaag gtggcaccgc aggcgtgccc ggcgcagtgc     300
tcttgctcgg gcagcacagt ggactgtcac gggctggcgc tgcgcagcgt gcccaggaat     360
atcccccgca acaccgagag actggattta aatgaaaata acatcacaag aattacgaag     420
acagattttg ctggtcttag acatctaaga gttcttcagc ttatggagaa taagattagc     480 accatgaaa gaggagcatt ccaggatctt aaagaactag agagactgcg tttaaacaga     540
aatcaccttc agctgttccc tgagttgctg tttcttggga ctgcgaagct atacaggctt     600
gatctcagtg aaaaccaaat tcaggcaatc ccaaggaaag ctttccgtgg ggcagttgac     660
ataaaaaatt tgcaactgga ttacaaccag atcagctgta ttgaagatgg ggcattcagg     720
```

```
gctctccggg acctggaagt gctcactctc aacaataaca acattactag actttctgtg    780
gcaagtttca accatatgcc taaacttagg acttttcgac tgcattcaaa caacctgtat    840
tgtgactgcc acctggcctg gctctccgac tggcttcgcc aaaggcctcg ggttggtctg    900
tacactcagt gtatgggccc ctcccacctg agaggccata atgtagccga ggttcaaaaa    960
cgagaatttg tctgcagtgg tcaccagtca tttatggctc cttcttgtag tgttttgcac   1020
tgccctgccg cctgtacctg tagcaacaat atcgtagact gtcgtgggaa aggtctcact   1080
gagatcccca caaatcttcc agagaccatc acagaaatac gtttggaaca gaacacaatc   1140
aaagtcatcc ctcctggagc tttctcacca tataaaaagc ttagacgaat tgacctgagc   1200
aataatcaga tctctgaact tgcaccagat gcttttccaag gactacgctc tctgaattca   1260
cttgtcctct atggaaataa aatcacagaa ctccccaaaa gtttatttga aggactgttt   1320
tccttacagc tcctattatt gaatgccaac aagataaact gccttcgggt agatgctttt   1380
caggatctcc acaacttgaa ccttctctcc ctatatgaca acaagcttca gaccatcgcc   1440
aaggggacct tttcacctct tcgggccatt caaactatgc atttggccca gaaccccttt   1500
atttgtgact gccatctcaa gtggctagcg gattatctcc ataccaaccc gattgagacc   1560
agtggtgccc gttgcaccag cccccgccgc ctggcaaaca aaagaattgg acagatcaaa   1620
agcaagaaat tccgttgttc agctaaagaa cagtatttca ttccaggtac agaagattat   1680
cgatcaaaat taagtggaga ctgctttgcg gatctggctt gccctgaaaa gtgtcgctgt   1740
gaaggaacca cagtagattg ctctaatcaa aagctcaaca aatcccgga gcacattccc   1800
cagtacactg cagagttgcg tctcaataat aatgaattta ccgtgttgga agccacagga   1860
atctttaaga aacttcctca attacgtaaa ataaacttta gcaacaataa gatcacagat   1920
attgaggagg gagcatttga aggagcatct ggtgtaaatg aaatacttct tacgagtaat   1980
cgtttggaaa atgtgcagca taagatgttc aagggattgg aaagcctcaa aactttgatg   2040
ttgagaagca atcgaataac ctgtgtgggg aatgacagtt tcataggact cagttctgtg   2100
cgtttgcttt ctttgtatga taatcaaatt actacagttg caccaggggc atttgatact   2160
ctccattctt tatctactct aaacctcttg gccaatcctt ttaactgtaa ctgctacctg   2220
gcttggttgg gagagtggct gagaaagaag agaattgtca cgggaaatcc tagatgtcaa   2280
aaaccatact tcctgaaaga aatacccatc caggatgtgg ccattcagga cttcacttgt   2340
gatgacggaa atgatgacaa tagttgctcc ccactttctc gctgtcctac tgaatgtact   2400
tgcttggata cagtcgtccg atgtagcaac aagggtttga aggtcttgcc gaaaggtatt   2460
ccaagagatg tcacagagtt gtatctggat ggaaaccaat ttacactggt tcccaaggaa   2520
ctctccaact acaaacattt aacacttata gacttaagta caacagaat aagcacgctt   2580
tctaatcaga gcttcagcaa catgacccag ctcctcacct taattcttag ttacaaccgt   2640
ctgagatgta ttcctcctcg caccttttgat ggattaaagt ctcttcgatt actttctcta   2700
catggaaatg acatttctgt tgtgcctgaa ggtgctttca atgatctttc tgcattatca   2760
catctagcaa ttggagccaa ccctctttac tgtgattgta acatgcagtg gttatccgac   2820
tgggtgaagt cggaatataa ggagcctgga attgctcgtt gtgctggtcc tggagaaatg   2880
gcagataaac ttttactcac aactccctcc aaaaaattta cctgtcaagg tcctgtggat   2940
gtcaatattc tagctaagtg taaccoctgc ctatcaaatc cgtgtaaaaa tgatggcaca   3000
tgtaatagtg atccagttga cttttaccga tgcacctgtc catatggttt caaggggcag   3060
gactgtgatg tcccaattca tgcctgcatc agtaacccat gtaaacatgg aggaacttgc   3120
```

```
cacttaaagg aaggagaaga agatggattc tggtgtattt gtgctgatgg atttgaagga    3180
gaaaattgtg aagtcaacgt tgatgattgt gaagataatg actgtgaaaa taattctaca    3240
tgtgtcgatg gcattaataa ctacacatgc ctttgcccac ctgagtatac aggtgagttg    3300
tgtgaggaga agctggactt ctgtgcccag gacctgaacc cctgccagca cgattcaaag    3360
tgcatcctaa ctccaaaggg attcaaatgt gactgcacac cagggtacgt aggtgaacac    3420
tgcgacatcg atttttgacga ctgccaagac aacaagtgta aaaacggagc ccactgcaca    3480
gatgcagtga acggctatac gtgcatatgc cccgaaggtt acagtggctt gttctgtgag    3540
ttttctccac ccatggtcct ccctcgtacc agccctgtg ataattttga ttgtcagaat     3600
ggagctcagt gtatcgtcag aataaatgag ccaatatgtc agtgtttgcc tggctatcag    3660
ggagaaaagt gtgaaaaatt ggttagtgtg aattttataa acaaagagtc ttatcttcag    3720
attccttcag ccaaggttcg gcctcagacg aacataacac ttcagattgc cacagatgaa    3780
gacagcggaa tcctcctgta taagggtgac aaagaccata tcgcggtaga actctatcgg    3840
gggcgtgttc gtgccagcta tgacaccggc tctcatccag cttctgccat ttacagtgtg    3900
gagacaatca atgatggaaa cttccacatt gtggaactac ttgccttgga tcagagtctc    3960
tctttgtccg tggatggtgg gaaccccaaa atcatcacta acttgtcaaa gcagtccact    4020
ctgaattttg actctccact ctatgtagga ggcatgccag ggaagagtaa cgtggcatct    4080
ctgcgccagg cccctgggca gaacggaacc agcttccacg gctgcatccg gaacctttac    4140
atcaacagtg agctgcagga cttccagaag gtgccgatgc aaacaggcat tttgcctggc    4200
tgtgagccat gccacaagaa ggtgtgtgcc catggcacat gccagcccag cagccaggca    4260
ggcttcacct gcgagtgcca ggaaggatgg atggggcccc tctgtgacca acggaccaat    4320
gacccttgcc ttggaaataa atgcgtacat ggcacctgct tgcccatcaa tgcgttctcc    4380
tacagctgta agtgcttgga gggccatgga ggtgtcctct gtgatgaaga ggaggatctg    4440
tttaacccat gccaggcgat caagtgcaag cacgggaagt gcaggctttc aggtctgggg    4500 cagcccctact gtgaatgcag cagtggatac acggggggaca gctgtgatcg agaaatctct    4560
tgtcgagggg aaaggataag agattattac caaaagcagc agggctatgc tgcttgccaa    4620
acaaccaaga aggtgtcccg attagagtgc agaggtgggt gtgcaggagg gcagtgctgt    4680
ggaccgctga ggagcaagcg gcggaaatac tctttcgaat gcactgacgg ctcctccttt    4740
gtggacgagg ttgagaaagt ggtgaagtgc ggctgtacga ggtgtgtgtc ctaaacacac    4800
tcccggcagc tctgtctttg gaaaaggttg tatacttctt gaccatgtgg gactaatgaa    4860
tgcttcatag tggaaatatt tgaaatatat tgtaaaatac agaacagact tatttttatt    4920
atgagaataa agactttttt tctgcatttg                                     4950
```